(12) United States Patent
Suk et al.

(10) Patent No.: US 10,238,635 B2
(45) Date of Patent: Mar. 26, 2019

(54) N-CARBAMOYLATED URETHANE FOR TREATING A NEUROINFLAMMATORY DISEASE

(71) Applicants: Kyungpook National University Industry—Academic Cooperation Foundation, Daegu (KR); KYUNGPOOK NATIONAL UNIVERSITY HOSPITAL, Daegu (KR)

(72) Inventors: Kyoungho Suk, Daegu (KR); Gyun Jee Song, Daegu (KR); Youngpyo Nam, Daegu (KR); Myungjin Jo, Daegu (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 0 days.

(21) Appl. No.: 15/495,841

(22) Filed: Apr. 24, 2017

(65) Prior Publication Data
US 2018/0028502 A1    Feb. 1, 2018

(30) Foreign Application Priority Data

Apr. 22, 2016    (KR) ........................ 10-2016-0049177

(51) Int. Cl.
A61K 31/42    (2006.01)
(52) U.S. Cl.
CPC .................................. A61K 31/42 (2013.01)
(58) Field of Classification Search
CPC ..................................................... A61K 31/42
See application file for complete search history.

(56) References Cited

PUBLICATIONS

Mayo Clinic, (alzheinner's prevention: Does not exist?), Mar. 20, 2018.*
Benveniste et al., Immunological aspects of microglia: relevance to Alzheimer's disease, Neurochemistry International 39 (2001) pp. 381-391, 11 pgs.
Knott et al., "Inflammatory Regulators in Parkinson's Disease: iNOS, Lipocortin-1, and Cyclooxygenases-1 and -2," Molecular and Cellular Neuroscience 16, 724-739, Sep. 2000, 16 pgs.
Mejia et al., "Minocycline Reduces Traumatic Brain Injury-mediated Caspase-1 Activation, Tissue Damage, and Neurological Dysfunction," Rapid Communication, Neurosurgery, vol. 48, No. 6, pp. 1393-1401, Jun. 2001, 9 pgs.
Song et al., Abstract for Phenotypic screening to identify small-molecule inhibitor of glia-mediated neuroinflammation, Neuroscience 2015 held in Oct. 2015, Chicago, USA.
Tomas et al., "Protective effects of lysophosphatidic acid (LPA) on chronic ethanol-induced injuries to the cytoskeleton and on glucose uptake in rat astrocytes," Journal of Neurochemistry, 2003, 87, 220-229, Oct. 2003, 10 pgs.
Van Den Bosch et al., "Minocycline delays disease onset and mortality in a transgenic model of ALS," Neuropharmacology and Neurotoxicology, NeuroReport vol. 13, No. 8, pp. 1067-1070, Jun. 12, 2002, 4 pgs.
Yrjanheikki et al., "Tetracyclines inhibit microglial activation and are neuroprotective in global brain ischemia," Proc. Natl. Acad. Sci. USA, vol. 95, pp. 15769-15774, Dec. 1998, Neurobiology, 6 pgs.
Glass et al., "Mechanisms Underlying Inflammation in Neurodegeneration," Cell 140, 918-934, Mar. 19, 2010, 17 pgs.
P.F. Durrenberger et al., "Common mechanisms in neurodegeneration and neuroinflammation: a BrainNet Europe gene expression microarray study," J Neural Transm, DOI 10.1007/s00702-014-1293-0, Aug. 13, 2014, 14 pgs.
Frank-Cannon et al., "Does neuroinflammation fan the flame in neurodegenerative diseases?," Molecular Neurodegeneration 2009, 4:47, Nov. 16, 2009, 13 pgs.
Ransohoff, "How neuroinflammation contributes to neurodegeneration," Science Magazine vol. 353 Issue 6301, Aug. 19, 2016, 8 pgs.
Russo et al., "Inflammatory neuroprotection following traumatic brain injury," Science Magazine vol. 353 Issue 6301, Aug. 19, 2016, 1 pg.
Clark et al., "The Immune System and Neuroinflammation as Potential Sources of Blood-Based Biomarkers for Alzheirner's Disease, Parkinson's Disease, and Huntington's Disease," ACS Chem. Neurosci. 2016, 520-527, Apr. 5, 2016, 8 pgs.
McKenzie et al., "Neuroinflammation as a Common Mechanism Associated with the Modifiable Risk Factors for Alzheimer's and Parkinson's Diseases," Current Aging Science, 2017, 10, 158-176, Mar. 2017, 19 pgs.

* cited by examiner

Primary Examiner — Zohreh A Fay
(74) Attorney, Agent, or Firm — Martin & Ferraro, LLP

(57) ABSTRACT

There is provided a composition for treating a neuroinflammatory disease comprising a N-carbamoylated urethane compound which has an effect of inhibiting the activity of microglia or astrocytes and the production of nitric oxide (NO) and TNF-α, and suppressing the expression of IL-1β And iNOS genes. There is also provide a method for treating a neuroinflammatory disease, the method comprising the step of administering a N-carbamoylated urethane compound. Due to its above mentioned effects, the N-carbamoylated urethane compound according to the present invention can be useful for the treatment of neuroinflammatory diseases.

3 Claims, 8 Drawing Sheets
Specification includes a Sequence Listing.

compound 1

N-CARBAMOYLATED URETHANE FOR TREATING A NEUROINFLAMMATORY DISEASE

CROSS-REFERENCE TO RELATED APPLICATIONS

The present application claims priority to Korean Patent Application No. 10-2016-0049177 filed on Apr. 22, 2016. The disclosures of the said application are incorporated by reference as if fully set forth herein.

BACKGROUND

Technical Field

The present invention relates to a composition for treating a neuroinflammatory disease comprising a N-carbamoylated urethane compound. In particular, the present invention relates to a composition for treating a neuroinflammatory disease, the composition comprising a N-carbamoylated urethane compound which has an effect of inhibiting the activity of microglia or astrocytes and the production of nitric oxide (NO) and TNF-α, and suppressing the expression of IL-1β and iNOS genes.

Discussion of the Background

Inflammatory reactions are caused by various inflammatory mediators and immune cells in the local blood vessels and body fluids when there are tissue (cell) damage or infections with foreign agents (such as bacteria, fungi, viruses, and various allergens), while exhibiting a series of complex physiological responses such as the activation of enzymes, the secretion of inflammatory mediators, the infiltration of body fluids, the migration of cells and the destruction of tissues; and external symptoms such as erythema, edema, fever, and pain. Under normal conditions, the inflammatory reactions remove the external infectious agents and regenerate the damaged tissues to recover the normal function of the afflicted organism. However, when the external infectious agents or antigens are not removed or the inflammatory reactions occur excessively or maintain continuously due to internal substances, damages to mucosal layers of tissues may occur and thus lead to diseases such as cancer in some cases.

Recently, it has been found that an inflammatory reaction is one of the main mechanisms causing neurodegeneration. In other words, microglia, which are immune cells present in the central nervous system, can be activated by various exogenous and endogenous substances. Activated microglial cells then produce and release substances including inflammatory cytokines such as TNF-α and IL-1β, nitric oxide, prostaglandins, and superoxides. The production of these substances induces an immune response in the short term, while its excessive or sustained production induces the death of adjacent neurons and eventually leads to neurodegeneration. In addition, since substances released from apoptotic neurons may cause microglial cells to re-activate, neurodegeneration falls into a constant vicious circle. In fact, it has been reported that various neurodegenerative diseases such as Alzheimer's disease, Parkinson's disease, Huntington's disease, Lou Gehrig's disease, Creutzfelt-Jakob Disease (CJD) and multiple sclerosis are associated with the activation of microglial cells.

Indeed, activated microglial cells in the brain of patients with Parkinson's disease have been observed (See Hunot et al., 1999; Knott et al., 2000), while the similar observation was detected in animal models of Parkinson's disease by using 1-methyl-4-phenyl-1,2,3,6-tetratetrahydropyridine (MPTP) (See Kohutnicka et al., 1998; Liberatore et al., 1999; Dehmer et al., 2000; Wu et al., 2002). In addition to Parkinson's disease, activated microglial cells have been also observed in various neurological diseases or disorders such as Huntington's disease (See Chen et al., 2000; Tomas et al., 2003; Wang et al., 2003), Alzheimer's disease (Benvensite et al., 2001), Lou Gehrig's disease (See Kriz et al., 2002; Van Den Bosch et al., 2002; Zhu et al., 2002), and localized and ischemic stroke (See Yrjaeikki et al., 1998; Arvin et al., 2001), as well as in traumatic head injuries (See Sanches Meijia et al., 2001).

Microglial cells are ones which perform the primary immune function in the central nervous system. They maintain their shape of thin, long branches and thin cell bodies. Upon the existence of endogenous or exogenous toxins, microglial cells change into their activated shape of thick, short branches and fat cell bodies in order to protect neurons from those toxins. Unlike normal microglial cells, activated microglial cells perform phagocytosis actively, proliferate, and produce inflammatory mediators by inducing the expression of the genes of cytokines (such as TNF-α, IL-1β and IL-6), chemokines, iNOS (inducible nitric oxide synthase), and COX-2 (cyclooxygenase-2). In one aspect, the activation of microglial cells leads to the removal of damaged cells and the protection of neurons from externally invading agents such as bacteria and viruses. In another aspect, however, nitric oxide produced by iNOS and prostaglandins, TNF-α and the like produced by COX-2 are toxic to neurons. As a result, the activation of microglial cells may aggravate the neuronal damage.

In conclusion, since the neuroinflammatory response, which is represented by the activation of microglial cells among various types of nerve cells, plays an important pathological role in various nerve tissue damage, it is suggested that it would be possible to inhibit the neural damages by suppressing the activation of inflammation caused by microglial cells, leading to the development of clinically applicable preventive and therapeutic agents for a neuroinflammatory disease.

SUMMARY

Accordingly, the present inventors have researched on substances capable of fundamentally treating a wide range of neuroinflammatory diseases by inhibiting the activation of microglial cells and the associated neuroinflammatory reaction in various ways. As a result, the present inventors have found that N-carbamoylated urethane compounds as disclosed herein inhibit neuroinflammation, thereby completing the present invention.

Hence, in one embodiment, the presently disclosed subject matter provides a pharmaceutical composition for treating a neuroinflammatory disease, the composition comprising a compound represented by Chemical Formula 1 or a pharmaceutically acceptable salt thereof as an active ingredient:

[Chemical Formula 1]

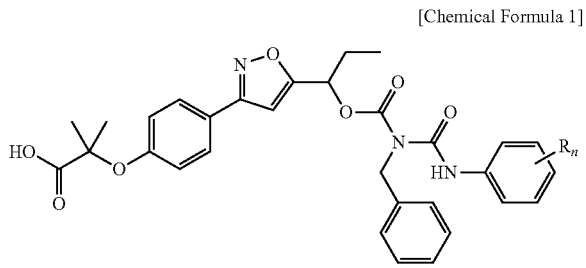

wherein n is 1 or 2,

R is selected from the group consisting of C1-C4 alkoxy, C1-C4 alkyl unsubstituted or substituted by halogen, halogen, hydrogen, and 3,4-methylenedioxy.

In another embodiment, the presently disclosed subject matter provides a food composition for alleviating a neuroinflammatory disease, the composition comprising a compound represented by Chemical Formula 1 as an active ingredient:

[Chemical Formula 1]

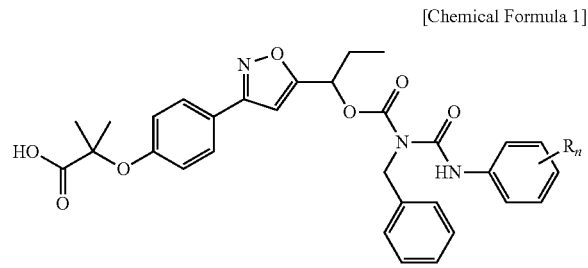

wherein n is 1 or 2,

R is selected from the group consisting of C1-C4 alkoxy, C1-C4 alkyl unsubstituted or substituted by halogen, halogen, hydrogen, and 3,4-methylenedioxy.

In yet another embodiment, the presently disclosed subject matter provides a method for treating a neuroinflammatory disease, the method comprising the step of administering a compound represented by Chemical Formula 1 or a pharmaceutically acceptable salt thereof in an amount effective to treat a neuroinflammatory disease in a subject:

[Formula 1]

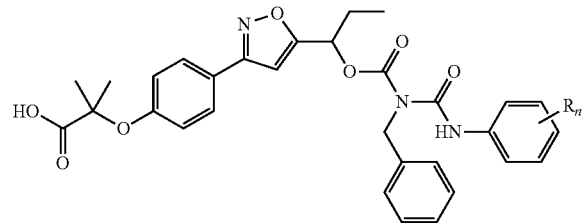

wherein n is 1 or 2,

R is selected from the group consisting of C1-C4 alkoxy, C1-C4 alkyl unsubstituted or substituted by halogen, halogen, hydrogen, and 3,4-methylenedioxy.

In still yet another embodiment, the presently disclosed subject matter provides said method for treating a neuroinflammatory disease wherein the compound of Chemical Formula 1 is selected from the group consisting of:

2-(4-(5-(1-((benzyl(phenylcarbamoyl)carbamoyl)oxy)propyl) isoxazol-3-yl)phenoxy)-2-methylpropanoic acid, 2-(4-(5-(1-((benzyl((2-methoxyphenyl)carbamoyl)carbamoyl) oxy)propyl)isoxazol-3-yl)phenoxy)-2-methylpropanoic acid, 2-(4-(5-(1-((benzyl((3-methoxyphenyl)carbamoyl)carbamoyl) oxy)propyl)isoxazol-3-yl)phenoxy)-2-methylpropanoic acid, 2-(4-(5-(1-((benzyl((4-methoxyphenyl)carbamoyl)carbamoyl) oxy)propyl)isoxazol-3-yl)phenoxy)-2-methylpropanoic acid, 2-(4-(5-(1-((benzyl((4-methylphenyl)carbamoyl)carbamoyl) oxy)propyl)isoxazol-3-yl)phenoxy)-2-methylpropanoic acid, 2-(4-(5-(1-((benzyl((4-trifluoromethylphenyl)carbamoyl) carbamoyl)oxy)propyl)isoxazol-3-yl)phenoxy)-2-methylpropanoic acid, 2-(4-(5-(1-((benzyl((4-chloromethylphenyl)carbamoyl) carbamoyl)oxy)propyl)isoxazol-3-yl)phenoxy)-2-methylpropanoic acid, 2-(4-(5-(1-((benzyl((4-n-butylmethylphenyl)carbamoyl) carbamoyl)oxy)propyl)isoxazol-3-yl)phenoxy)-2-methylpropanoic acid, 2-(4-(5-(1-((benzyl((3,4-dimethoxymethylphenyl)carbamoyl) carbamoyl)oxy)propyl)isoxazol-3-yl)phenoxy)-2-methylpropanoic acid, 2-(4-(5-(1-((benzyl((3,5-dimethoxymethylphenyl)carbamoyl) carbamoyl)oxy)propyl)isoxazol-3-yl)phenoxy)-2-methylpropanoic acid and 2-(4-(5-(1-((benzyl((3,5-methylenedioxymethylphenyl) carbamoyl)carbamoyl)oxy)propyl)isoxazol-3-yl)phenoxy)-2-methylpropanoic acid.

In still further embodiment, the presently disclosed subject matter provides said method for treating a neuroinflammatory disease wherein the neuroinflammatory disease is selected from the group consisting of inflammatory brain disease, multiple sclerosis, neuroblastoma, stroke, Alzheimer's disease, Parkinson's disease, Lou Gehrig's disease, Huntington's disease, Creutzfeldt-Jakob disease, post-traumatic stress disorder, depression, schizophrenia, and amyotrophic lateral sclerosis.

In still yet further embodiment, the presently disclosed subject matter provides said method wherein the compound represented by Chemical Formula 1 or a pharmaceutically acceptable salt thereof is effective for prophylactically treating the neuroinflammatory disease.

DETAILED DESCRIPTION OF THE ILLUSTRATED EMBODIMENTS

Figure 1:
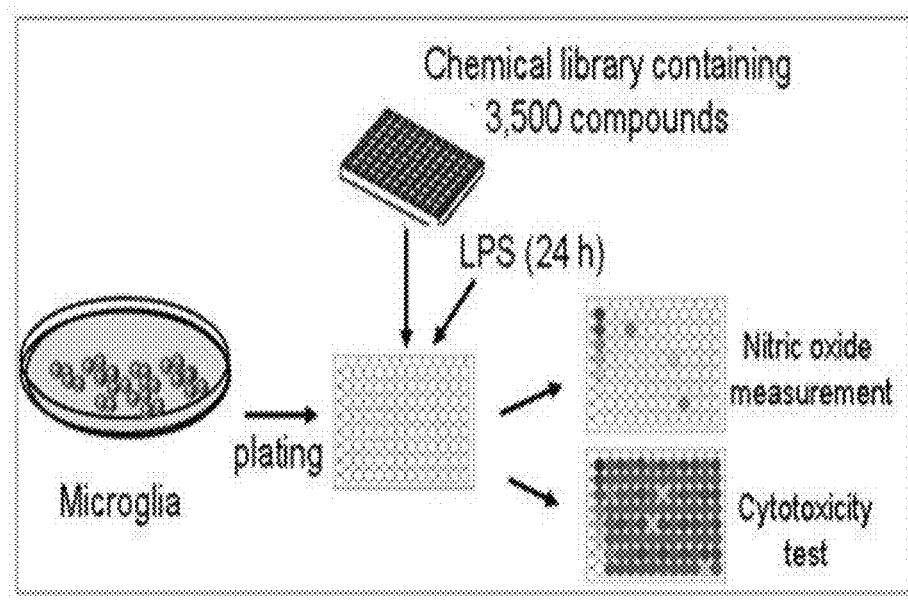
FIG. 1 is a schematic diagram showing a process of selecting a substance that inhibits the production of nitric oxide (NO) in microglia cells using high throughput screening (HTS).

The presently disclosed subject matter will be described more fully hereinafter with reference to the accompanying Examples and Drawings, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments of those skilled in the art.

It will be apparent to one skilled in the art that various modifications and variations can be made in the present invention without departing from the spirit or scope of the invention. Thus, it is intended that the present invention covers the modifications and variations of the presently described embodiments come within the scope of the appended claims and their equivalents.

In one embodiment, the presently disclosed subject matter provides a pharmaceutical composition for treating a neuroinflammatory disease, the composition comprising a compound represented by Chemical Formula 1 or a pharmaceutically acceptable salt thereof as an active ingredient:

[Chemical Formula 1]

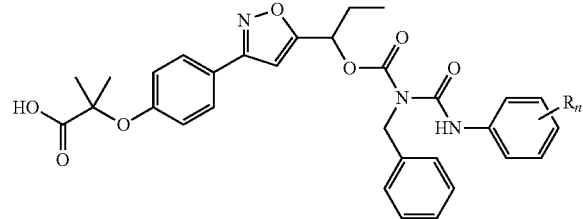

wherein
n is 1 or 2,
R is selected from the group consisting of C1-C4 alkoxy, C1-C4 alkyl unsubstituted or substituted by halogen, halogen, hydrogen, and 3,4-methylenedioxy.

As used herein, the term "pharmaceutically acceptable salt" is not limited as long as it forms an addition salt with the above compound, and includes salts derived from pharmaceutically acceptable inorganic acids, organic acids, or bases. Examples of suitable acid addition salts include inorganic acids such as sulfuric acid, hydrochloric acid, nitric acid, phosphoric acid, bromic acid, perchloric acid, hydroiodic acid and the like; organic carboxylic acids such as oxalic acid, citric acid, succinic acid, tartaric acid, formic acid, acetic acid, trichloroacetic acid, trifluoroacetic acid, glycolic acid, benzoic acid, lactic acid, fumaric acid, maleic acid and salicylic acid; sulfonic acids such as methanesulfonic acid, ethanesulfonic acid, benzenesulfonic acid, toluene-p-sulfonic acid, naphthalene-2-sulfonic acid and the like. Examples of suitable base addition salts include alkali metal or alkaline earth metal salts formed by lithium, sodium, potassium, calcium, magnesium and the like; amino acid salts of lysine, arginine, guanidine and the like; base addition salts formed with organic salts such as dicyclohexylamine, N-methyl-D-glucamine, tris(hydroxymethyl)methylamine, diethanolamine, choline, triethylamine and the like.

The compound of the Chemical Formula 1 according to the present invention can be converted into a salt thereof by a conventional method, while the preparation of the salt can be easily carried out by those skilled in the art based on the structure of the presently disclosed compounds without any particular explanation.

The compound of the Chemical Formula 1 according to the present invention includes tautomeric isomers thereof. The compound according to the present invention has one asymmetric center, and thus enantiomers thereof are also included. All such isomers and mixtures thereof are included within the scope of the present invention. The present invention also includes a prodrug of the above Chemical Formula 1. As used herein, the term "prodrug" means a functional derivative of the compound of the Chemical Formula 1, which can be easily converted so as to exhibit its effect in a living body. Conventional procedures for the selection and preparation of suitable prodrug derivatives are disclosed in the literatures (See Design of Prodrug, ed. H. Bundgaard, 1985) Preferably, the compound of the Chemical Formula 1 according to the present invention includes, but is not limited to:

2-(4-(5-(1-((benzyl(phenylcarbamoyl)carbamoyl)oxy)propyl) isoxazol-3-yl)phenoxy)-2-methylpropanoic acid,
2-(4-(5-(1-((benzyl((2-methoxyphenyl)carbamoyl)carbamoyl) oxy)propyl)isoxazol-3-yl)phenoxy)-2-methylpropanoic acid,
2-(4-(5-(1-((benzyl((3-methoxyphenyl)carbamoyl)carbamoyl) oxy)propyl)isoxazol-3-yl)phenoxy)-2-methylpropanoic acid,
2-(4-(5-(1-((benzyl((4-methoxyphenyl)carbamoyl)carbamoyl) oxy)propyl)isoxazol-3-yl)phenoxy)-2-methylpropanoic acid,
2-(4-(5-(1-((benzyl((4-methylphenyl)carbamoyl)carbamoyl) oxy)propyl)isoxazol-3-yl)phenoxy)-2-methylpropanoic acid,
2-(4-(5-(1-((benzyl((4-trifluoromethylphenyl)carbamoyl) carbamoyl)oxy)propyl)isoxazol-3-yl)phenoxy)-2-methylpropanoic acid,
2-(4-(5-(1-((benzyl((4-chloromethylphenyl)carbamoyl) carbamoyl)oxy)propyl)isoxazol-3-yl)phenoxy)-2-methylpropanoic acid,
2-(4-(5-(1-((benzyl((4-n-butylmethylphenyl)carbamoyl) carbamoyl)oxy)propyl)isoxazol-3-yl)phenoxy)-2-methylpropanoic acid,
2-(4-(5-(1-((benzyl((3,4-dimethoxymethylphenyl)carbamoyl) carbamoyl)oxy)propyl)isoxazol-3-yl)phenoxy)-2-methylpropanoic acid,
2-(4-(5-(1-((benzyl((3,5-dimethoxymethylphenyl)carbamoyl) carbamoyl)oxy)propyl)isoxazol-3-yl)phenoxy)-2-methylpropanoic acid and
2-(4-(5-(1-((benzyl((3,5-methylenedioxymethylphenyl) carbamoyl)carbamoyl)oxy)propyl)isoxazol-3-yl)phenoxy)-2-methylpropanoic acid.

As used herein, as long as it is being a disease caused by the inflammation of the nervous system, the neuroinflammatory disease may include, but are not limited to, multiple sclerosis, neuroblastoma, stroke, Alzheimer's disease, Parkinson's disease, Lou Gehrig's disease, Huntington's disease, Creutzfeldt-Jakob disease, post-traumatic stress disorder, depression, schizophrenia, and amyotrophic lateral sclerosis.

According to one embodiment of the present invention, the compound of the Chemical Formula 1 was found to reduce the activation of microglial cells under LPS (lipopolysaccharide)-induced inflammatory conditions, and to inhibit the expression of the genes of the inflammatory cytokines TNF-α, IL-1β and iNOS, and suppresses the production of nitric oxide (NO). In addition, the compound of the Chemical Formula 1 was shown to reduce the release of NO and TNF-α from astrocytes under LPS-induced inflammatory conditions, and to promote an anti-inflammatory phenotypic change in astrocytes. Accordingly, it was verified that the pharmaceutical composition comprising the compound of the Chemical Formula 1 or a pharmaceutically acceptable salt thereof as an active ingredient may be useful for preventing or treating a neuroinflammatory disease via its effect of inhibiting inflammation and reducing the activation of microglial cells.

In addition, the composition for treating a neuroinflammatory disease in accordance with the present invention may be prepared into various types of formulation according to the route of administration by a method known in the art together with pharmaceutically acceptable carriers. The term "pharmaceutically acceptable" refers to a non-toxic composition which is physiologically acceptable and, when administered to humans, does not interfere with the action of the active ingredient and does not normally cause an allergic or similar reaction such as gastrointestinal disorders, dizziness, or the like. Such carriers include all kinds of solvents, dispersion media, oil-in-water or water-in-oil emulsions, aqueous compositions, liposomes, microbeads and microsomes.

In the case of a parenteral administration, the composition of the present invention for treating a neuroinflammatory disease may be formulated by known methods in the art into the form of an injectable, transdermal or nasal inhalation preparation in combination with suitable parenteral carriers. In the case of an injectable preparation, it must be sterilized and protected from the contamination of microorganisms such as bacteria and fungi. Examples of suitable carriers for an injectable preparation include, but are not limited to, solvents or dispersion media containing water, ethanol, polyols (e.g., glycerol, propylene glycol and liquid polyethylene glycol), mixtures thereof and/or vegetable oils. More preferably, the suitable carriers include Hank's solution, Ringer's solution, phosphate buffered saline (PBS) containing triethanolamine or isotonic solutions such as sterilized water for injection, 10% ethanol, 40% propylene glycol and 5% dextrose. In order to protect the injectable preparation from microbial contamination, various antibacterial and antifungal agents such as paraben, chlorobutanol, phenol, sorbic acid, thimerosal and the like may be further included. In addition, the injectable preparation may further comprise an isotonic agent such as sugar and sodium chloride in most cases.

Preparations of transdermal administration may include ointments, creams, lotions, gels, solutions for external use, pastes, liniments, and air-rolls. As used herein, the term "transdermal administration" means that an effective amount of the active ingredient contained in the composition of the present invention is delivered into the skin by topically administering the composition of the present invention to the skin. For instance, the composition of the present invention may be prepared into an injectable formulation and administered by pricking the skin lightly with a 30 gauge thin needle or by directly applying it to the skin. These preparations or formulations are described in Remington's Pharmaceutical Science, 15th Edition, 1975, Mack Publishing Company, Easton, Pa., which is a commonly known formulary in pharmaceutical chemistry.

In the case of inhalation dosage forms, the composition according to the present invention may be conveniently delivered in an aerosol spray form from pressurized packs or nebulisers using suitable propellants, for example dichlorofluoromethane, trichlorofluoromethane, dichlorotetrafluoroethane, carbon dioxide or other suitable gases. In the case of a pressurized aerosol, the dosage unit may be determined by providing a valve that delivers a metered amount. For example, gelatin capsules and cartridges for use in an inhaler or insufflator may be formulated to contain a powder mixture of a compound and a suitable powder base such as lactose and starch.

Other pharmaceutically acceptable carriers can be found in Remington's Pharmaceutical Sciences, 19th ed., Mack Publishing Company, Easton, Pa., 1995.

The pharmaceutical composition for treating a neuroinflammatory disease in accordance with the present invention may further contain one or more buffers (e.g., saline or PBS), carbohydrates (e.g., glucose, mannose, sucrose or dextran), antioxidants, bacteriostatic agents, chelating agents (e.g., EDTA or glutathione), adjuvants (e.g., aluminum hydroxide), suspending agents, thickening agents, and/or preservatives.

In addition, the pharmaceutical composition of the present invention for treating a neuroinflammatory disease may be variously formulated using methods known in the art so as to accomplish rapid, sustained or delayed release of its active ingredient upon being administered to a mammal subject. The composition of the present invention may also be administered in combination with one or more a known compound having an effect of treating a neuroinflammatory disease.

In another embodiment, the presently disclosed subject matter provides a food composition for ameliorating a neuroinflammatory disease, the composition comprising a compound of the following Chemical Formula 1 as an active ingredient:

[Chemical Formula 1]

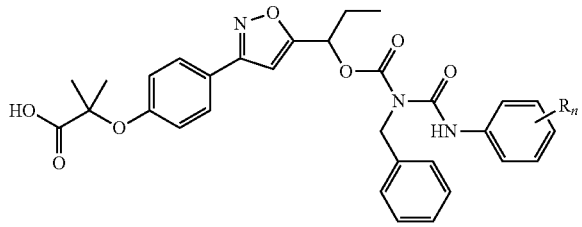

wherein n is 1 or 2,

R is selected from the group consisting of C1-C4 alkoxy, C1-C4 alkyl unsubstituted or substituted by halogen, halogen, hydrogen, and 3,4-methylenedioxy.

The food composition comprising the Chemical Formula 1 according to the present invention includes all forms of functional foods, nutritional supplements, health foods, and food additives. These types of functional foods can be prepared in various forms in accordance with conventional methods known in the art.

For example, as health foods, the food composition per se of the present invention may be prepared and ingested in the form of teas, juices, and drinks, while also being in the types of granules, capsules, and powders. In addition, the food composition of the present invention can be prepared in the form of a composition by mixing with a known anti-inflammatory substance or active ingredient.

Further, as functional foods, the food composition of the present invention may be added to beverages (including alcoholic beverages), fruits and their processed foods (such as canned fruits, bottled fruits, jam, marmalade), fish, meat and their processed foods (e.g., ham, sausage, corn beef), breads and noodles (e.g., udon, buckwheat noodles, ramen, spaghetti, macaroni), juices, various drinks, cookies, taffies, dairy products (e.g., butter, cheese), edible vegetable oils, margarines, vegetable proteins, retort foods, frozen foods, or various kinds of seasoning (e.g., soybean paste, soy sauce, sauce).

The preferable content of the food composition according to the present invention is not limited to, but is preferably 0.01 to 50% by weight based on the total weight of the final food product. In order to use the food composition of the present invention in the form of a food additive, it may be prepared in the form of powder or concentrate.

The composition of the present invention, which comprises the compound of Chemical Formula 1 or pharmaceutically acceptable salt thereof as an active ingredient, reduces the activation of microglial cells under LPS (lipopolysaccharide)-induced inflammatory conditions, and inhibits the expression of the genes of the inflammatory cytokines TNF-α, IL-1β and iNOS, and suppresses the production of nitric oxide (NO). In addition, the composition of the present invention reduces the release of NO and TNF-α from astrocytes under LPS-induced inflammatory conditions, and induces an anti-inflammatory phenotypic change in astrocytes. Thus, the composition of the present invention can be effectively used for treating a neuroinflammatory disease.

In still another embodiment, the presently disclosed subject matter provides a method for treating a neuroinflammatory disease, the method comprising the step of administering a compound represented by Chemical Formula 1 or a pharmaceutically acceptable salt thereof in an amount effective to treat a neuroinflammatory disease in a subject:

[Formula 1]

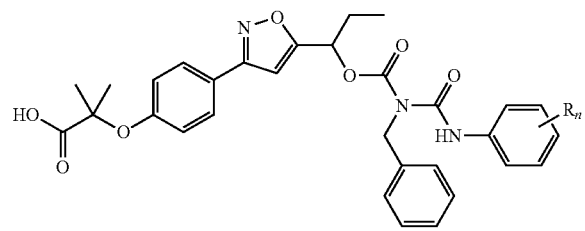

wherein n is 1 or 2,

R is selected from the group consisting of C1-C4 alkoxy, C1-C4 alkyl unsubstituted or substituted by halogen, halogen, hydrogen, and 3,4-methylenedioxy.

In still yet another embodiment, the presently disclosed subject matter provides said method for treating a neuroinflammatory disease wherein the compound of Chemical Formula 1 is selected from the group consisting of:

2-(4-(5-(1-((benzyl(phenylcarbamoyl)carbamoyl)oxy)propyl) isoxazol-3-yl)phenoxy)-2-methylpropanoic acid, 2-(4-(5-(1-((benzyl((2-methoxyphenyl)carbamoyl)carbamoyl) oxy)propyl)isoxazol-3-yl)phenoxy)-2-methylpropanoic acid, 2-(4-(5-(1-((benzyl((3-methoxyphenyl)carbamoyl)carbamoyl) oxy)propyl)isoxazol-3-yl)phenoxy)-2-methylpropanoic acid, 2-(4-(5-(1-((benzyl((4-methoxyphenyl)carbamoyl)carbamoyl) oxy)propyl)isoxazol-3-yl)phenoxy)-2-methylpropanoic acid, 2-(4-(5-(1-((benzyl((4-methylphenyl)carbamoyl)carbamoyl) oxy)propyl)isoxazol-3-yl)phenoxy)-2-methylpropanoic acid, 2-(4-(5-(1-((benzyl((4-trifluoromethylphenyl)carbamoyl) carbamoyl) oxy) propyl)isoxazol-3-yl)phenoxy)-2-methylpropanoic acid, 2-(4-(5-(1-((benzyl((4-chloromethylphenyl)carbamoyl) carbamoyl) oxy) propyl)isoxazol-3-yl)phenoxy)-2-methylpropanoic acid, 2-(4-(5-(1-((benzyl((4-n-butylmethylphenyl)carbamoyl) carbamoyl)oxy)propyl)isoxazol-3-yl)phenoxy)-2-methylpropanoic acid, 2-(4-(5-(1-((benzyl((3,4-dimethoxymethylphenyl)carbamoyl) carbamoyl)oxy)propyl)isoxazol-3-yl)phenoxy)-2-methylpropanoic acid, 2-(4-(5-(1-((benzyl((3,5-dimethoxymethylphenyl)carbamoyl) carbamoyl)oxy)propyl)isoxazol-3-yl)phenoxy)-2-methylpropanoic acid and 2-(4-(5-(1-((benzyl((3,5-methylenedioxymethylphenyl) carbamoyl)carbamoyl)oxy)propyl)isoxazol-3-yl)phenoxy)-2-methylpropanoic acid.

In still further embodiment, the presently disclosed subject matter provides said method for treating a neuroinflammatory disease wherein the neuroinflammatory disease is selected from the group consisting of inflammatory brain disease, multiple sclerosis, neuroblastoma, stroke, Alzheimer's disease, Parkinson's disease, Lou Gehrig's disease, Huntington's disease, Creutzfeldt-Jakob disease, post-traumatic stress disorder, depression, schizophrenia, and amyotrophic lateral sclerosis.

As used herein, the term "effective amount" refers to an amount that, when administered to a subject, leads to the effect of treating a neuroinflammatory disease. The effective amount varies depending on the route of administration, the severity of disease, sex, weight, age of the subject and the like. One skilled in the art where the presently described subject matter belongs will be able to determine the appropriate effective amount of a compound represented by Chemical Formula 1 or a pharmaceutically acceptable salt thereof according to the present invention to be administered in view of the above mentioned various factors.

The term "subject" refers to an animal, preferably a mammal which includes a human, while including animal-derived cells, tissues, organs and the like. The subject may be a patient in need of the above mentioned effect.

As used herein, the term "treating" broadly refers to the improvement of a neuroinflammatory disease, or the amelioration of symptoms derived from a neuroinflammatory disease, while including, without limitation, curing, substantially preventing or prophylactically treating, and improving a neuroinflammatory disease conditions; and relieving, curing or preventing one or more of the symptoms resulting from said neuroinflammatory disease.

In still yet further embodiment, the presently disclosed subject matter provides said method wherein the compound represented by Chemical Formula 1 or a pharmaceutically acceptable salt thereof is effective for prophylactically treating the neuroinflammatory disease.

EXAMPLES

Hereinafter, the present invention will be described in detail.

However, the following examples are illustrative of the present invention only, and the contents of the present invention are not limited to the following examples.

<Experimental Method>

1. Test Substance

LPS (lipopolysaccharide) and IL-4 were purchased from Sigma-Aldrich (St. Louis, Mo., USA) and R&D system (Minneapolis, Minn., USA), respectively.

2. Cell Culture

BV-2 cells, a murine microglial cell line, were cultured in Dulbecco's modified Eagle's medium (DMEM) containing 5% heat-inactivated FBS and 50 μg/ml gentamicin at 37° C. Rat microglial HAPI cells and mouse primary astrocytes were cultured in DMEM (10% FBS, 10 U/ml penicillin, 10 μg/ml streptomycin) at 37° C. All animals and experimental procedures were approved by the Institutional Review Board of Kyungpook National University School of Pharmacy and were carried out in accordance with the NIH Guide for the Care and Use of Laboratory Animals. All animals were maintained under temperature- and humidity-controlled conditions.

The mouse primary microglial cells were cultured under mild conditions according to known methods. In brief, the forebrains of 3-5 day-old C57BL/6 mice were harvested and mechanically pulverized using a nylon mesh. The cells were seeded onto a poly-L-lysine-coated flasks and then cultured. After in vitro culture of 10-14 days, the microglial cells were isolated from the mixed glial cultures by shaking for 6 hours at 200 rpm. Astrocytes remained attached to the bottom of the culture flask were used for the following experiments.

3. High Throughput Screening

The production of nitric oxide (NO) was estimated by measuring the amount of nitrite, which is a NO metabolite. The BV-2 cells (40,000 cells/well in 96-well plates) were treated with 100 ng/ml of LPS in the presence or absence of the compounds from the library. At the end of a 24 hour incubation period, 50 μl of the cell culture media was mixed with an equal volume of a Griess reagent in each well. The light absorbance was measured at 540 nm, while a standard curve was generated using sodium nitrite.

4. Assessment of Cell Viability

Cell viability was assessed using MTT assay. After treatment with LPS and the compounds, the culture solution was aspirated and removed. MTT (0.5 mg/ml in PBS) was added to the cells and incubated at 37° C. for 4 hours. The resulting formazan was dissolved in DMSO. The absorbance was determined at 570 nm using a microplate reader.

5. ELISA for TNF-α

The BV-2 cells or astrocytes were treated with LPS and Compound 1, followed by culturing for 24 hours. The TNF-α levels in the culture media were measured using a rat monoclonal anti-mouse TNF-α antibody as a primary antibody and a goat anti-mouse TNF-α antibody as a secondary antibody.

6. Traditional and Real-Time RT-PCR

Total RNA was extracted from microglial cells or brain tissues using TRIZOL reagent (Invitrogen, Carlsbad, Calif., USA). Reverse transcription (RT) was performed using Superscript II reverse transcriptase (Invitrogen) and Oligo (dT) primers. Traditional polymerase chain reaction (PCR) amplification was performed using specific primer sets at annealing temperature 55-60° C. for 20-30 cycles. PCR was performed using C1000 Touch Thermal Cycler. For the PCR product analysis, 10 μl of each PCR reaction was electrophoresed on 1% agarose gel and detected under ultraviolet light.

Real-time RT-PCR was performed using Perfect Real-Time One Step SYBR Primer Script RT-PCR Kit (Takara Bio, Otsu, Shiga, Japan).

The primer sequences were designed based on published cDNA sequences (See Table 1).

TABLE 1

Primers used for RT-PCR

| Target genes | Accession No. | Forward primer (5' → 3') | Reverse primer (3' → 5') |
|---|---|---|---|
| TNF-α | NM_013693.2 | CATCTTCTCAAAATTCGAGTGACAA (SEQ ID NO: 1) | ACTTGGGCAGATTGACCTCAG (SEQ ID NO: 2) |
| IL-1β | NM_008361.3 | GCAACTGTTCCTGAACTC (SEQ ID NO: 3) | CTCGGAGCCTGTAGTGCA (SEQ ID NO: 4) |
| iNOS | NM_010927.3 | CCCTTCCGAAGTTTCTGGCAGCAGC (SEQ ID NO: 5) | GGCTGTCAGAGCCTCGTGGCTTTGG (SEQ ID NO: 6) |
| Ym-1 | NM_009892 | GGGCATACCTTTATCCTGAG (SEQ ID NO: 7) | CCACTGAAGTCATCCATGTC (SEQ ID NO: 8) |
| GAPDH | NM_008084 | ACCACAGTCCATGCCATCAC (SEQ ID NO: 9) | TCCACCACCCTGTTGCTGTA (SEQ ID NO: 10) |

8. Animal Model of Neuroinflammation

LPS was intraperitoneally administered according to a conventionally known method for producing neuroinflammatory mouse model. All experiments were performed on C57BL/6 mice aged 9-11 weeks, and the animals were supplied from Koatech. In each experiment, the animals were divided into four groups (Group 1, vehicle-treated group; Group 2, Compound 1-treated group; Group 3, LPS & vehicle-treated group; Group 4, LPS & Compound 1-treated group). Compound 1 (2 mg/kg) was dissolved in saline containing 5% DMSO and 40% polyethylene glycol and administered intraperitoneally daily for 4 days. LPS (5 mg/kg) induced a neuroinflammatory animal model by intraperitoneally administering its single dose on the second day.

For histological analysis, 72 hours after the administration of LPS, the animals were anesthetized and perfused transcardially first with saline and then with 4% paraformaldehyde. The activity of microglial cells was evaluated using Iba-1 staining. At least three animals were included in each experimental group.

9. Immunostaining

The brains of the test animals were fixed with 4% paraformaldehyde for 72 hours. Fixed brains were treated with 30% sucrose for 72 hours. The brains were then cut into 12-μm-thick sagittal sections. The sectioned brain was permeabilized with 0.3% Triton X-100 and blocked with 1% BSA & 5% donkey serum for 1 hour at room temperature. The brain sections were treated overnight at 4° C. with rabbit polyclonal anti-Iba-1 primary antibody, followed by an 1 hour treatment with a secondary antibody at room temperature. Mounting and counterstaining were performed with an anti-fade mounting medium containing DAPI. The images of each section were taken using a CCD color video camera.

<Experimental Results>

Example 1

Screening of Anti-Inflammatory Small Molecules

Microglia are immune cells residing in the brain which play a very important role in the defense mechanism of an organism. However, the uncontrolled inflammatory activation of microglia has been observed in many neurodegenerative diseases. Activated microglial cells play a central role in neuroinflammation by releasing various neurotoxic factors such as TNF-α, nitric oxide (NO), and reactive oxygen species. In order to find potent anti-inflammatory substances, the present inventors used high throughput screening to determine low molecular weight substances which inhibit LPS-induced NO production in a microglial BV-2 cells.

Figure 2A:
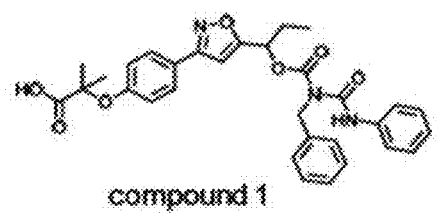
FIG. 2A shows the structure of Compound 1 selected via high throughput screening.
Figure 2B:
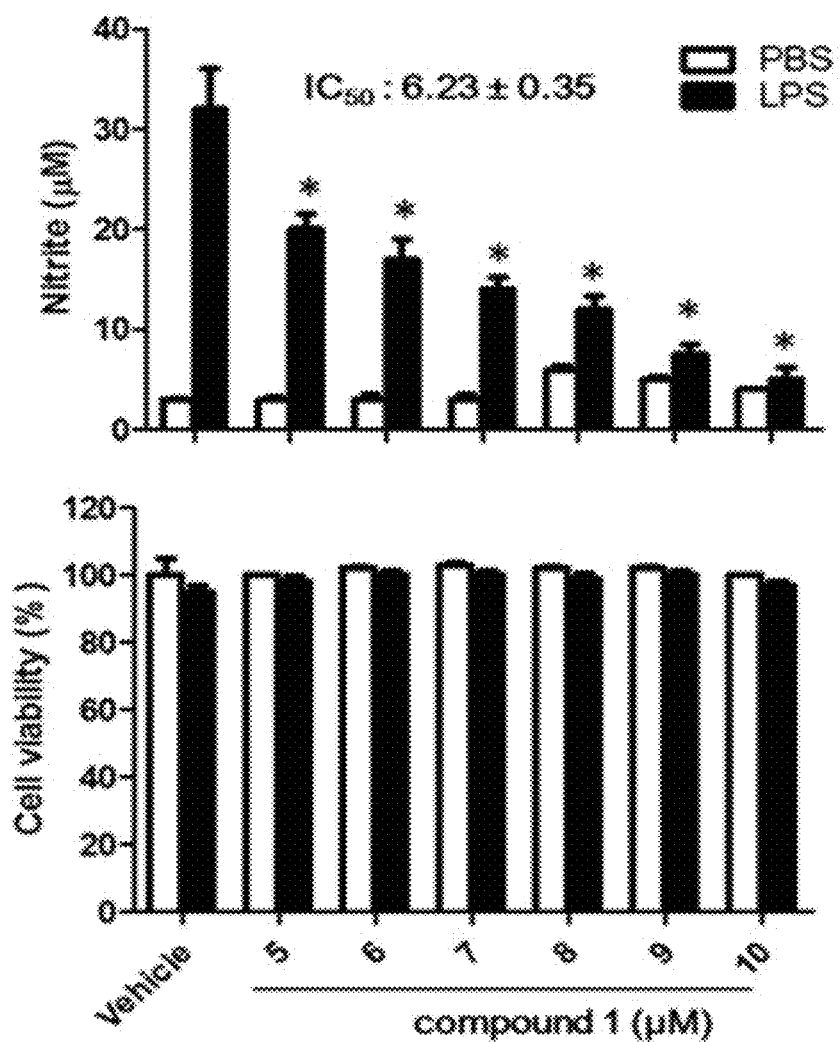
FIG. 2B shows the result of evaluating its cytotoxic and inhibitory effect on the production of NO.

Specifically, the BV-2 cells were cultured in 96-well plates and stimulated with LPS at a concentration of 100 ng/ml. The BV-2 cells stimulated with LPS were treated with 3,500 low molecular weight substances (FIG. 1). High-throughput screening was used to select a low molecular substance designated as "Compound 1" which is low in cytotoxicity and capable of effectively inhibiting NO production in microglial cells (FIG. 2A and FIG. 2B).

Example 2

Synthesis of Compound 1 and its derivatives

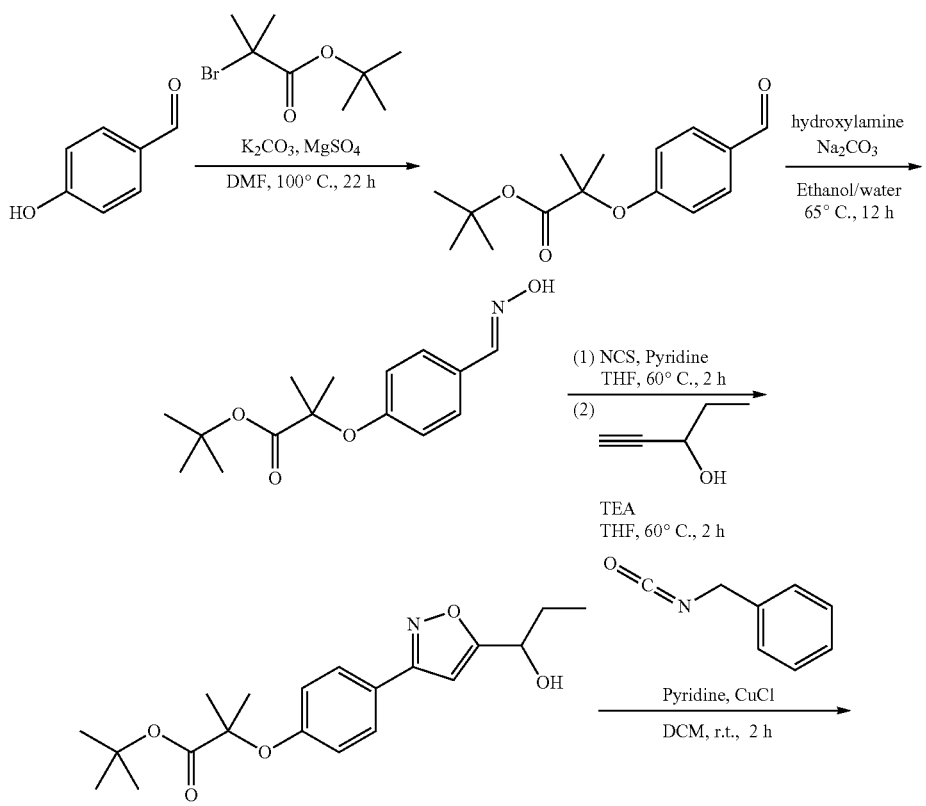

-continued

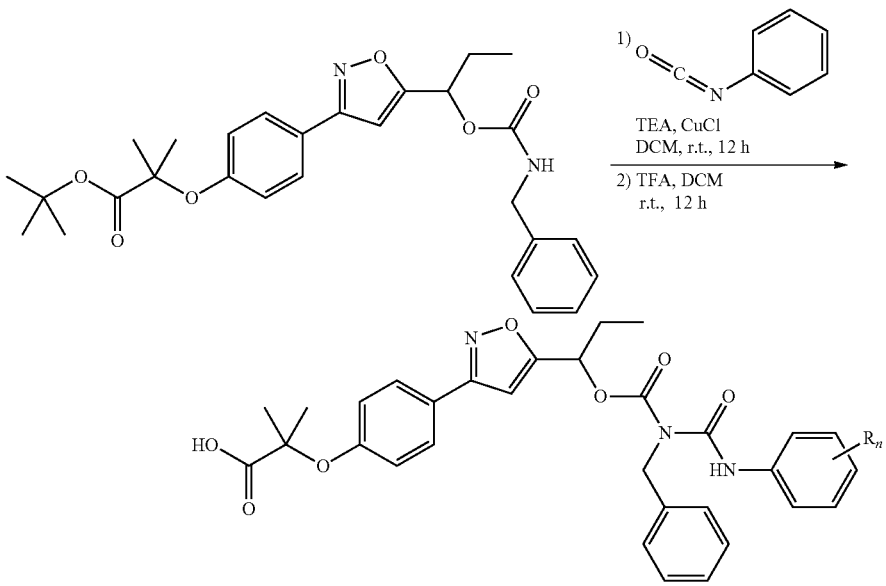

In the above Chemical Formula,
n is 1 or 2,
R is selected from the group consisting of C1-C4 alkoxy, C1-C4 alkyl unsubstituted or substituted by halogen, halogen, hydrogen and 3,4-methylenedioxy.

Compound 1

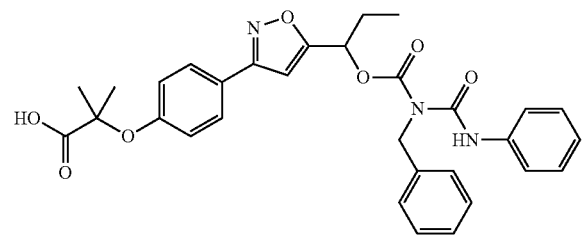

[M+H]$^+$=558.2235; M=558.2253; $^1$H NMR (500 MHz, DMSO-d6) δ 10.54 (s, 1H), 7.61 (d, J=8.6 Hz, 2H), 7.54 (d, J=8.6 Hz, 2H), 7.37-7.22 (m, 8H), 7.14-7.06 (m, 1H), 6.94 (d, J=7.8 Hz, 2H), 6.65 (s, 1H), 5.88 (t, J=6.4 Hz, 1H), 4.99 (s, 2H), 2.00-1.87 (m, 2H), 1.48 (s, 6H), 0.75 (t, J=7.2 Hz, 3H); $^{13}$C NMR (75 MHz, DMSO-d6) δ 169.6, 161.5, 158.2, 154.5, 151.3, 138.0, 137.8, 128.9, 128.4, 127.3, 127.2, 127.0, 123.9, 119.9, 118.2, 100.4, 80.1, 71.6, 46.8, 25.9, 25.7, 8.8

TABLE 2

Molecular weight and NMR data of Compound 1 derivatives

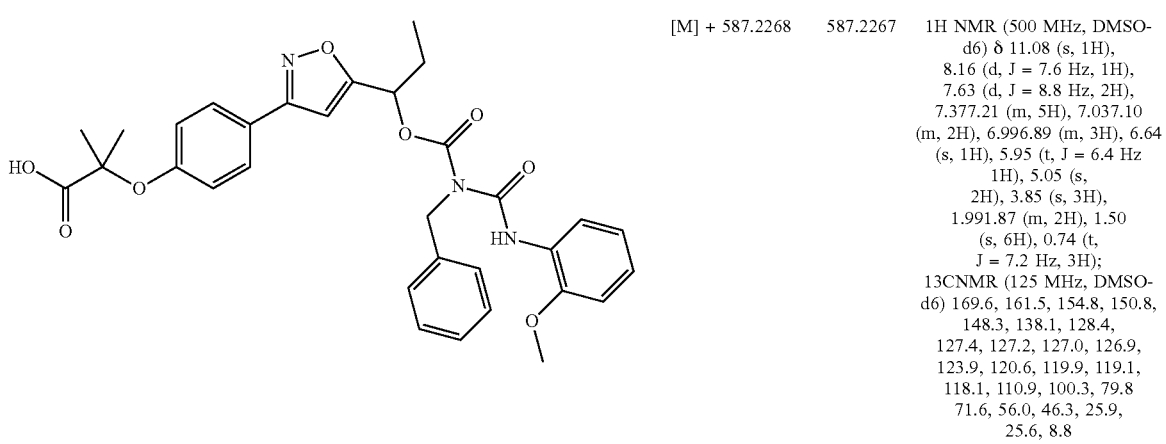

[M] + 587.2268   587.2267   1H NMR (500 MHz, DMSO-d6) δ 11.08 (s, 1H), 8.16 (d, J = 7.6 Hz, 1H), 7.63 (d, J = 8.8 Hz, 2H), 7.37.7.21 (m, 5H), 7.03.7.10 (m, 2H), 6.99.6.89 (m, 3H), 6.64 (s, 1H), 5.95 (t, J = 6.4 Hz 1H), 5.05 (s, 2H), 3.85 (s, 3H), 1.99.1.87 (m, 2H), 1.50 (s, 6H), 0.74 (t, J = 7.2 Hz, 3H); 13CNMR (125 MHz, DMSO-d6) 169.6, 161.5, 154.8, 150.8, 148.3, 138.1, 128.4, 127.4, 127.2, 127.0, 126.9, 123.9, 120.6, 119.9, 119.1, 118.1, 110.9, 100.3, 79.8 71.6, 56.0, 46.3, 25.9, 25.6, 8.8

TABLE 2-continued
Molecular weight and NMR data of Compound 1 derivatives
| | | | |
|---|---|---|---|
| 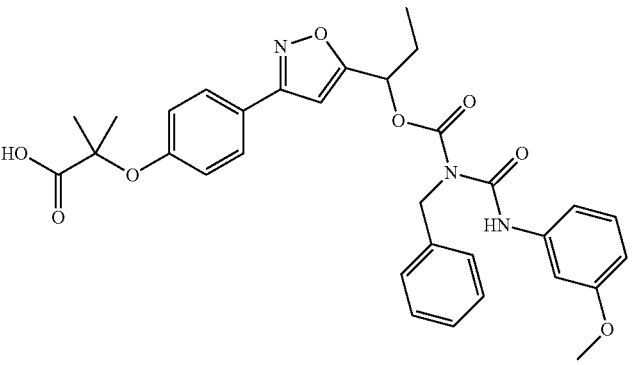 [SMILES: CCC(OC(=O)N(Cc1ccccc1)C(=O)Nc1cccc(OC)c1)c1cc(-c2ccc(OC(C)(C)C(=O)O)cc2)no1] | [M] + 587.2268 | 587.2261 | 1H NMR (500 MHz, DMSO-d6) δ 10.53 (s, 1H), 7.68 (d, J = 7.58 Hz, 2H), 7.39-7.19 (m, 7H), 7.10 (d, J = 8.1 Hz, 1H), 6.93 (d, J = 8.7 Hz, 2H), 6.72-6.65 (m, 2H), 5.89 (t, J = 6.2 Hz, 1H), 4.99 (s, 2H), 3.74 (s, 3H), 2.00-1.87 (m, 2H), 1.54 (s, 6H), 0.76 (t, J = 7.2 Hz, 3H); 13CNMR (125 MHz, DMSO-d6) δ 169.8, 161.4, 159.7, 157.4, 154.4, 151.3, 139.0, 138.0, 129.8, 128.4, 127.7, 127.2, 127.0, 120.7, 118.2, 112.0, 109.5, 105.4, 100.4, 79.0, 71.6, 55.1, 46.9, 25.9, 25.3, 8.8 |
| 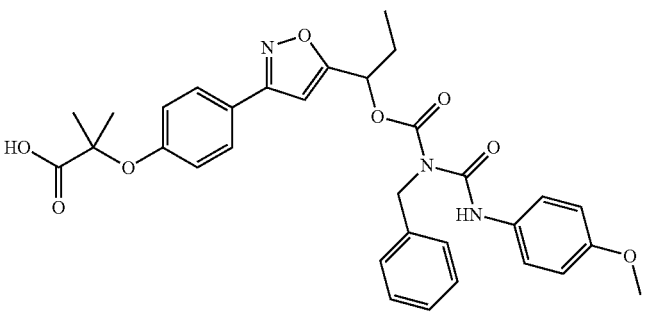 [SMILES: CCC(OC(=O)N(Cc1ccccc1)C(=O)Nc1ccc(OC)cc1)c1cc(-c2ccc(OC(C)(C)C(=O)O)cc2)no1] | [M] + 587.2268 | 587.2269 | 1H NMR (500 MHz, DMSO-d6) δ 10.37 (s, 1H), 7.63 (d, J = 8.6 Hz, 2H), 7.44 (d, J = 9.1 Hz, 2H), 7.37-7.24 (m, 5H), 6.93 (d, J = 8.8 Hz, 2H), 6.91 (d, J = 9.1 Hz, 2H), 6.66 (s, 1H), 5.87 (t, J = 6.4 Hz, 1H), 4.98 (s, 2H), 3.73 (s, 2H), 2.00-1.88 (m, 2H), 1.49 (s, 6H), 0.75 (t, J = 7.3 Hz, 3H); 13CNMR (125 MHz, DMSO-d6) δ 169.7, 161.5, 158.2, 155.8, 154.4, 151.4, 138.1, 130.7, 128.4, 127.4, 127.2, 127.0, 121.7, 119.8, 118.1, 114.0, 100.3, 71.5, 55.2, 46.8, 25.9, 25.7, 8.8 |
| 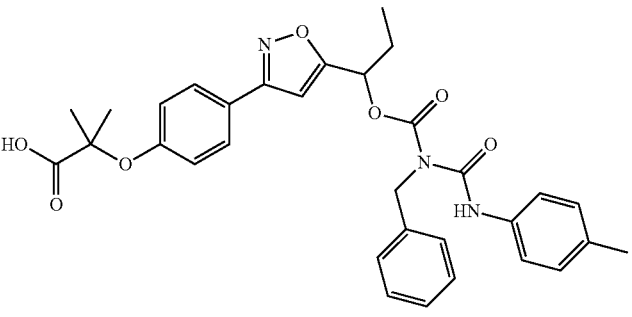 [SMILES: CCC(OC(=O)N(Cc1ccccc1)C(=O)Nc1ccc(C)cc1)c1cc(-c2ccc(OC(C)(C)C(=O)O)cc2)no1] | [M] + 571.2319 | 571.2316 | 1H NMR (500 MHz, DMSO-d6) δ 10.45 (s, 1H), 7.67 (d, J = 8.6 Hz, 2H), 7.42 (d, J = 8.3 Hz, 2H), 7.37-7.23 (m, 5H), 7.14 (d, J = 8.3 Hz, 2H), 6.92 (d, J = 8.8 Hz, 2H), 6.67 (s, 1H), 5.88 (t, J = 6.4 Hz, 1H), 4.98 (s, 2H), 2.26 (s, 3H), 2.01-1.88 (m, 2H), 1.53 (s, 6H), 0.75 (t, J = 7.2 Hz, 3H); 13CNMR (75 MHz, DMSO-d6) δ 169.8, 161.3, 157.5, 154.4, 151.3, 138.0, 135.2, 133.0, 129.3, 128.4, 127.7, 127.2, 127.0, 120.6, 119.9, 118.2, 100.4, 79.1, 71.5, 46.8, 25.9, 25.3, 20.4, 8.8 |

TABLE 2-continued

Molecular weight and NMR data of Compound 1 derivatives

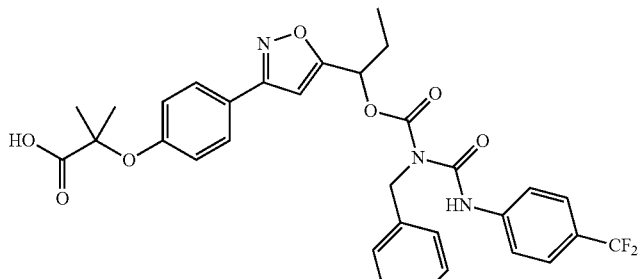

[M + H] + 626.2109   626.2103   1H NMR (500 MHz, DMSO-d6) δ 10.78 (s, 1H), 7.77 (d, J = 8.3 Hz, 2H), 7.70 (d, J = 8.3 Hz, 2H), 7.63 (d, J = 8.8 Hz, 2H), 7.38-7.23 (m, 5H), 6.94 (d, J = 8.8 Hz, 2H), 6.69 (s, 1H), 5.89 (t, J = 6.5 Hz, 1H), 4.99 (s, 2H), 2.00-1.89 (m, 2H), 1.50 (s, 6H), 0.76 (t, J = 7.3 Hz, 3H); 13CNMR, (75 MHz, DMSO-d6) δ 169.6, 161.5, 158.1, 154.3, 151.6, 141.5, 137.8, 128.4, 127.4, 127.3, 126.2, 126.2, 126.1, 119.8, 118.1, 110.9, 100.4, 79.9, 71.7, 48.6, 47.1, 25.9, 25.6, 8.8

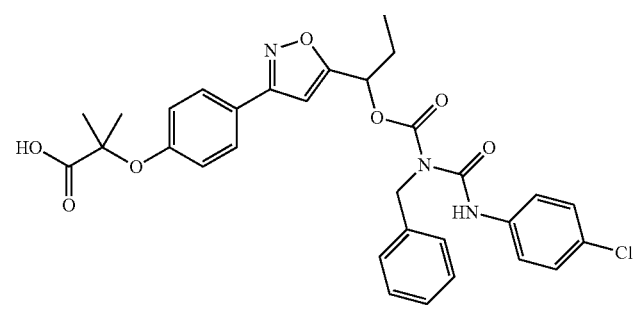 [SMILES: CCC(OC(=O)N(Cc1ccccc1)C(=O)Nc1ccc(Cl)cc1)c1cc(-c2ccc(OC(C)(C)C(=O)O)cc2)no1]

[M] + 591.1772   591.1775   1H NMR (500 MHz, DMSO-d6) δ 10.57 (s, 1H), 7.67 (d, J = 8.8 Hz, 2H), 7.59 (d, J = 9.1 Hz, 1H), 7.39 (d, J = 8.8 Hz, 1H), 7.36-7.24 (m, 5H), 6.93 (d, J = 8.8 Hz, 2H), 6.68 (s, 1H), 5.88 (t, J = 6.4 Hz, 1H), 4.98 (s, 2H), 1.99-1.88 (m, 2H), 1.53 (s, 6H), 0.75 (t, J = 7.3 Hz, 3H); 13CNMR (125 MHz, DMSO-d6) δ 169.7, 161.4, 157.7, 154.3, 151.4, 137.9, 136.8, 128.8, 128.4, 127.6, 127.6, 127.2, 127.0, 121.6, 120.4, 118.2, 100.4, 79.3, 71.6, 47.0, 25.9, 25.4, 8.8

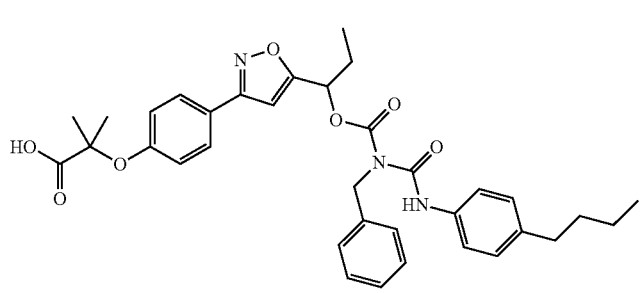 [SMILES: CCCCc1ccc(NC(=O)N(Cc2ccccc2)C(=O)OC(CC)c2cc(-c3ccc(OC(C)(C)C(=O)O)cc3)no2)cc1]

[M] + 613.2788   613.2790   1H NMR (500 MHz, DMSO-d6) δ 10.46 (s, 1H), 7.65 (d, J = 8.8 Hz, 2H), 7.43 (d, J = 8.6 Hz, 2H), 7.36-7.23 (m, 5H), 7.14 (d, J = 8.3 Hz, 2H), 6.92 (d, J = 8.8 Hz, 2H), 6.66 (s, 1H), 5.88 (t, J = 6.5 Hz, 1H), 4.99 (s, 2H), 2.56-2.48 (m, 3H), 1.99-1.87 (m, 2H), 1.57-1.46 (m, 8H), 1.32-1.25 (m, 2H), 0.88 (t, J = 7.5 Hz, 3H), 0.75 (t, J = 7.3 Hz, 3H); 13CNMR (75 MHz, DMSO-d6) δ 175.0, 169.7, 161.4, 157.9, 154.5, 151.3, 138.1, 138.0, 135.4, 128.7, 128.4, 127.6, 127.2, 127.0, 120.2, 120.0, 118.1, 100.4, 79.5, 71.5, 46.8, 34.2, 33.2, 25.9, 25.5, 21.7, 13.8, 8.8

TABLE 2-continued

Molecular weight and NMR data of Compound 1 derivatives

| [M]+ calc. | [M]+ found | NMR data |
|---|---|---|
| 617.2373 | 617.2378 | 1H NMR (500 MHz, DMSO-d6) δ 10.40 (s, 1H), 7.62 (d, J = 8.3 Hz, 2H), 7.38-7.23 (m, 5H), 7.19 (d, J = 1.5 Hz, 1H), 7.08 (d, J = 8.6 Hz, 1H), 6.91 (m, 3H), 6.65 (s, 1H), 5.87 (t, J = 6.4 Hz, 1H), 4.99 (s, 2H), 3.73 (s, 3H), 3.72 (s, 3H), 2.00-1.87 (m, 2H), 1.48 (s, 6H), 0.75 (t, J = 7.2 Hz, 3H); 13CNMR (75 MHz, DMSO-d6) δ 169.7, 161.5, 158.2, 154.5, 151.3, 148.7, 145.4, 138.1, 131.1, 128.4, 127.4, 127.2, 127.0, 119.7, 117.9, 112.0, 111.9, 105.2, 100.3, 71.5, 55.7, 55.5, 48.6, 46.7, 25.9, 25.7, 8.8 |
| 617.2373 | 617.2384 | 1H NMR (500 MHz, DMSO-d6) δ 10.51 (s, 1H), 7.61 (d, J = 8.6 Hz, 2H), 7.39-7.22 (m, 5H), 6.92 (d, J = 8.6 Hz, 2H), 6.78 (d, J = 2.2 Hz, 2H), 6.68 (s, 1H), 6.25 (s, 1H), 5.87 (t, J = 6.4 Hz, 1H), 4.97 (s, 2H), 3.71 (s, 6H), 1.96-1.89 (m, 2H), 1.47 (s, 6H), 0.75 (t, J = 7.3 Hz, 3H); 13CNMR (75 MHz, DMSO-d6) δ 169.6, 161.5, 160.6, 154.4, 151.2, 139.5, 138.0, 128.4, 127.3, 127.2, 127.0, 119.4, 118.0, 100.3, 97.9, 96.0, 80.3, 71.6, 69.8, 55.2, 46.9, 29.0, 25.9, 8.8 |
| 601.2060 | 601.2059 | 1H NMR (500 MHz, DMSO-d6) δ 10.39 (s, 1H), 7.67 (d, J = 8.8 Hz, 2H), 7.37-7.21 (m, 6H), 6.95-6.89 (m, 3H), 6.86 (t, J = 8.3 Hz, 1H), 6.66 (s, 1H), 6.00 (s, 2H), 5.87 (t, J = 6.4 Hz, 1H), 4.97 (s, 2H), 1.98-1.87 (m, 2H), 1.53 (s, 6H), 0.75 (t, J = 7.3 Hz, 3H); 13CNMR (75 MHz, DMSO-d6) δ 174.8, 169.8, 161.4, 157.5, 154.4, 151.4, 147.3, 143.6, 138.0, 132.0, 128.4, 127.7, 127.2, 127.0, 120.6, 118.2, 113.2, 108.1, 102.4, 101.2, 100.4, 79.1, 71.5, 46.8, 25.9, 25.3, 8.8 |

Example 3

Verification of the Anti-Inflammatory Effect of Compound 1 in Various Cell Types The present inventors confirmed the anti-neuroinflammatory effect of Compound 1, which was identified in Example 1, in the HAPI rat microglial cells and the RAW264.7 macrophage cells. The cells were cultured in 96-well plates, followed by treatment with various concentrations of Compound 1 with LPS, respectively. After 24 hours of such a treatment, NO release was examined.

Figure 3A:
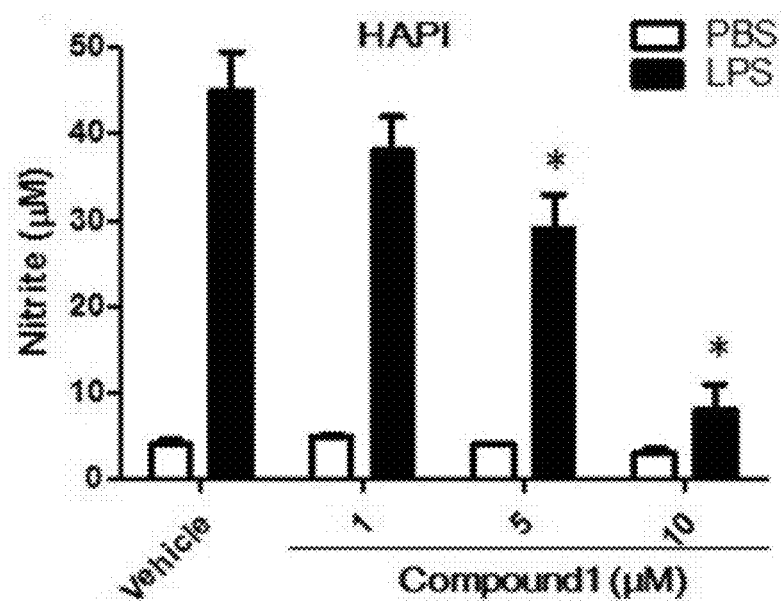
FIG. 3A shows the result of evaluating the inhibitory effect of Compound 1 on the NO production in the HAPI cell line.
Figure 3B:
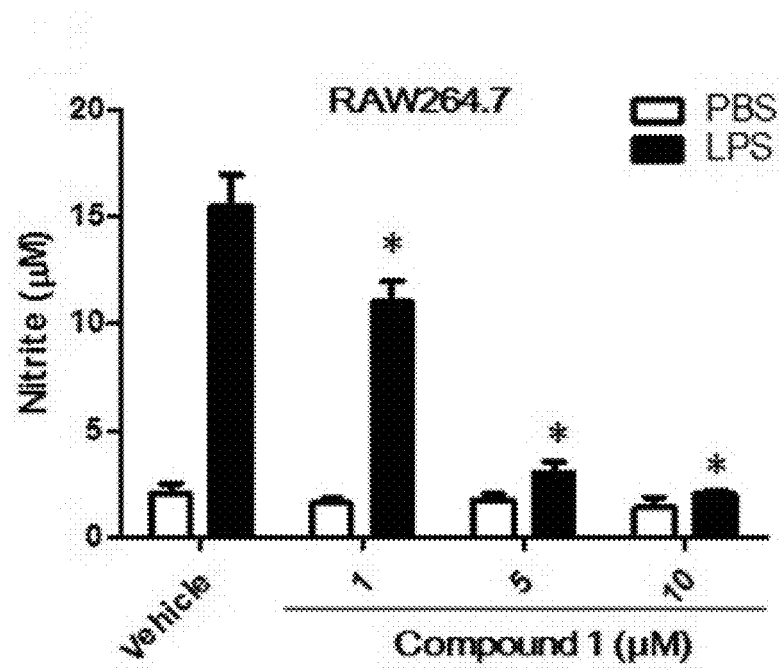
FIG. 3B shows the result of evaluating the inhibitory effect of Compound 1 on the NO production in the macrophage RAW264.7 cell line.

The result is shown in FIG. 3A and FIG. 3B. As shown in FIG. 3A and FIG. 3B, it was verified that Compound 1 inhibits the LPS-induced NO release in the microglial and macrophage cells in a dose-dependent manner. Further, the present inventors also evaluated the effect of the Compound 1 derivatives on LPS-induced NO release in the microglial cells, while the results are shown in the following Table 3:

TABLE 3

Inhibitory effect of Compound 1 and its derivatives on NO release

| Compound 1 derivatives (R=) | % inhibition of NO production |
|---|---|
| 2-methoxy | 20.9 |
| 3-methoxy | 25.6 |
| 4-methoxy | 46.7 |
| 4-methyl | 46.7 |
| 4-trifluoromethyl | 52.7 |
| 4-chloro | 67.8 |
| 4-n-butyl | 58.3 |
| 3,4-dimethoxy | 60.7 |
| 3,5-dimethoxy | 56.7 |
| 3,4-methylenedioxy | 74.6 |
| H (Compound 1) | 73.4 |

As can be seen in Table 3, it was found that the increased NO production induced by LPS (100 ng/ml) in the BV-2 microglial cells was inhibited by 10 μM of each of Compound 1 derivatives. While an increased NO production by LPS is designated as 100%, a suppressed amount of NO production by each derivative of Compound 1 is presented by its respective percentage.

Figure 4A:
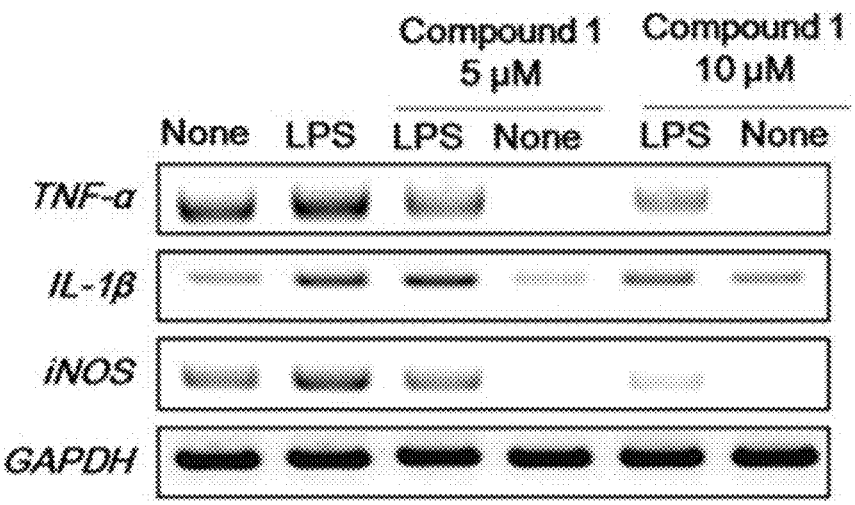
FIG. 4A shows the RT-PCR result of evaluating changes in the gene expression of inflammatory markers after treating microglial BV-2 cells with Compound 1.
Figure 4B:
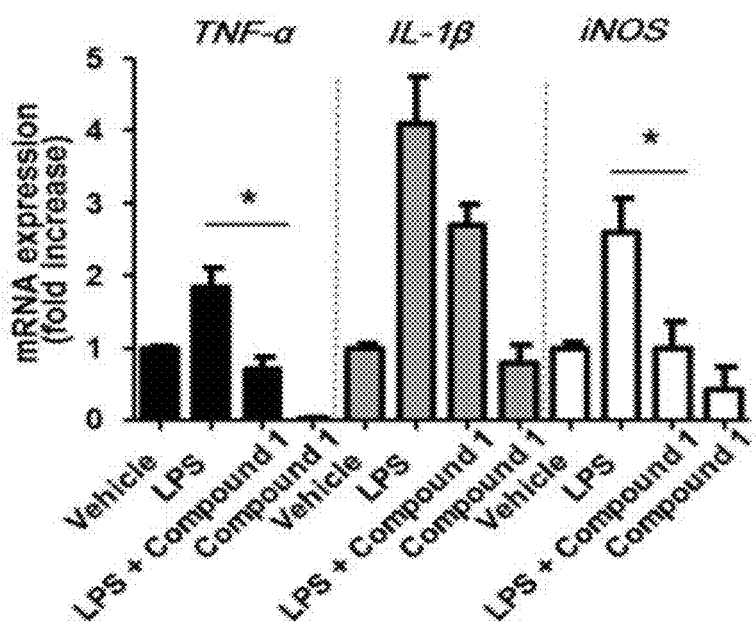
FIG. 4B shows the quantified result of FIG. 4A.
Figure 5A:
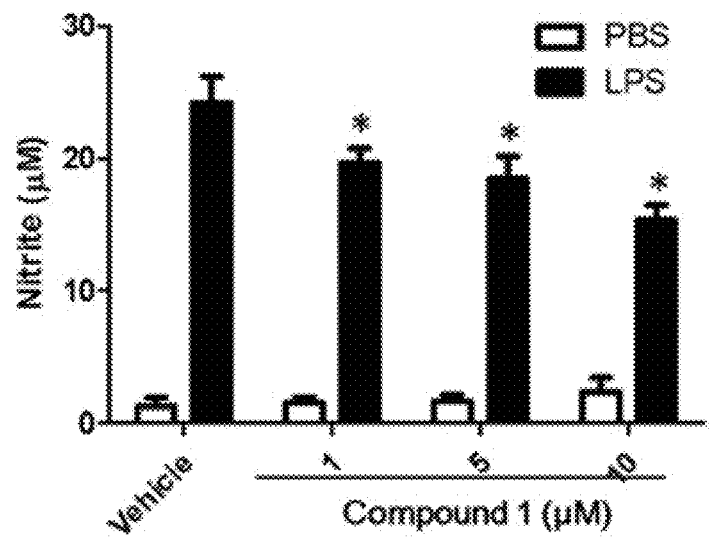
FIG. 5A shows changes in LPS-induced NO production when astrocytes were treated with Compound 1.
Figure 5B:
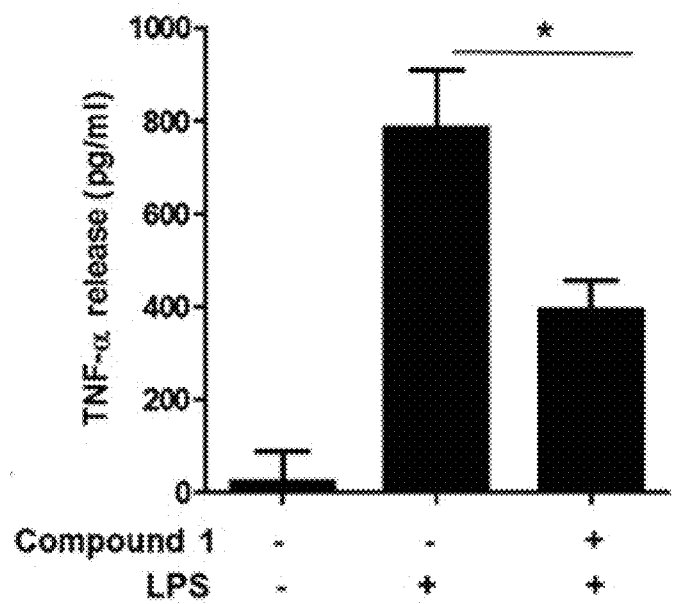
FIG. 5B shows changes in LPS-induced TNF-α production when astrocytes were treated with Compound 1.
Figure 5C:
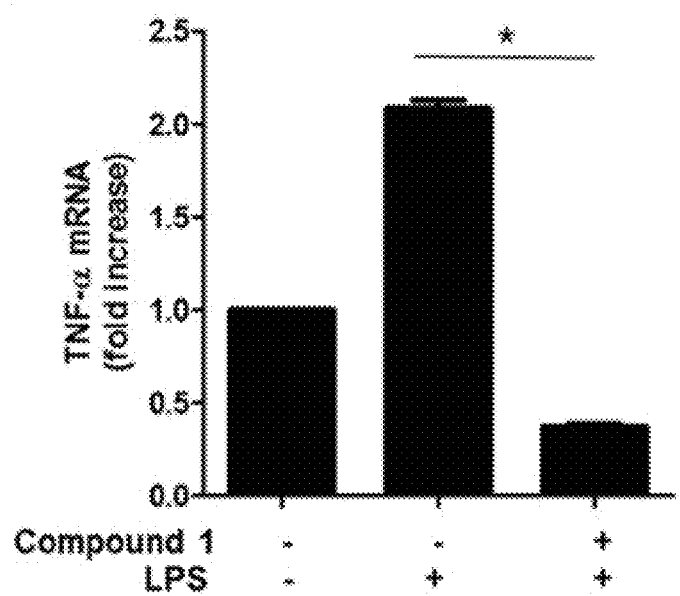
FIG. 5C shows changes in LPS-induced TNF-α mRNA expression when astrocytes were treated with Compound 1.
Figure 5D:
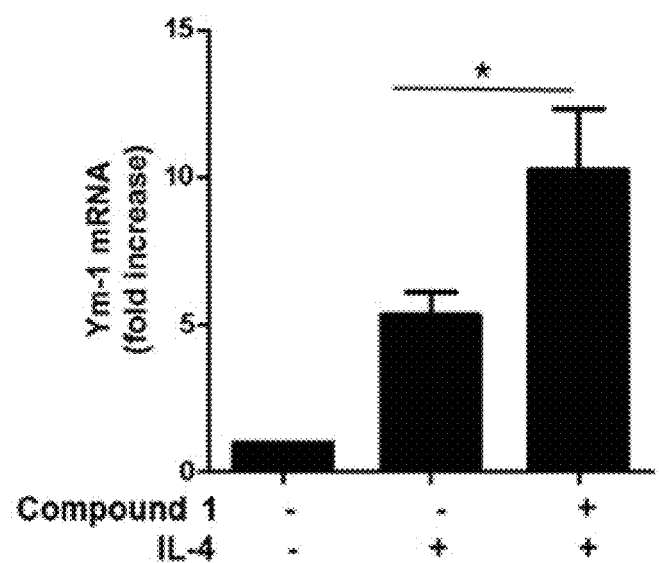
FIG. 5D shows changes in LPS-induced Ym-1 mRNA expression when astrocytes were treated with Compound 1.

Next, the effect of Compound 1 on the LPS-induced expression of pro-inflammatory mediators was examined in the BV-2 microglial cells. As shown in FIG. 4A and FIG. 4B, it was verified that the pre-treatment of the BV-2 microglial cells with Compound 1 significantly reduced the expression of inflammatory genes such as TNF-α, IL-1β and iNOS.

Example 4

Anti-Inflammatory Phenotypic Change by Compound 1 in Astrocytes

Astrocytes are a type of glial cells which are known to actively participate in the inflammatory reaction of the central nervous system under pathological conditions. Functionally polarized astrocytes have distinct gene expression patterns, along with different effector functions. The present inventors previously reported that reactive astrocytes generally exhibit anti-inflammatory gene expression and demonstrate neuroprotective activities. Thus, the present inventors examined the effect of Compound 1 on the functional polarization of astrocytes.

The results are shown in FIG. 5. As shown in FIG. 5A to FIG. 5D, it was verified that Compound 1 inhibited the LPS-induced NO and TNF-α production in astrocytes, while increasing the IL-4-induced Ym-1 expression. Thus, it is suggested from these results that the anti-neuroinflammatory effect of Compound 1 may be exerted through an anti-inflammatory phenotypic change for microglia and astrocytes.

Example 5

In Vivo Evaluation on the Anti-Neuroinflammatory Effect of Compound 1

(1) Next, the present inventors evaluated the effect of Compound 1 in the LPS-induced mouse neuroinflammation model. According to the previous study by the present inventors, it was found that, after the intraperitoneal administration of Compound 1 (2 mg/kg), its brain distribution was 0.19 μg/hr/ml with a half-life of 5.23 hr±1.52. Thus, for the in vivo functional study in the neuroinflammatory animal model, Compound 1 was intraperitoneally administered at a dose of 2 mg/kg.

Figure 6A:
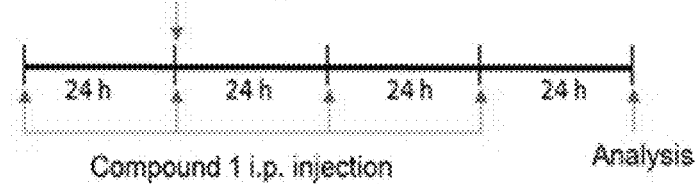
FIG. 6A shows the schedule of administration during the experiment for evaluating the effect of Compound 1 in an in vivo neuroinflammatory animal model.

As shown in FIG. 6A, Compound 1 was administered daily for four days in LPS-injected mice. The mice were then sacrificed, and the Iba-1 levels were analyzed as molecular markers of microglia activation (FIG. 6B).

Figure 6B:
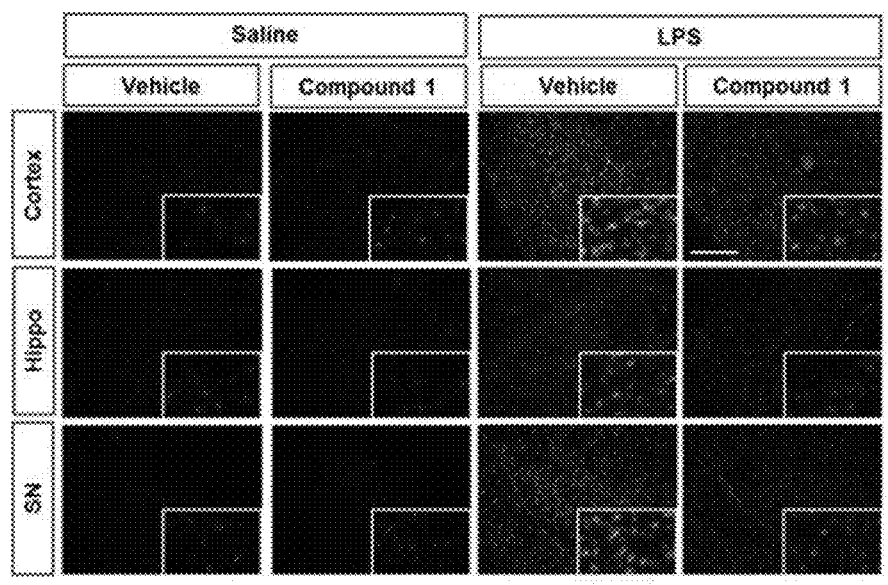
FIG. 6B shows the results of the immunostaining observation of the distribution of microglial cells which express Iba-1 in different locations of the brain.

As shown in FIG. 6B, upon observing the expression of the Iba-1 staining in the brain tissue sections, LPS injection dramatically increased the number of microglial cells (as measured by Iba-1 positive cells), whereas the LPS-induced microglial activation was significantly reduced in the Compound 1-treated group. The Iba-1-stained cells whose intensity values were above an arbitrarily defined threshold were counted from each of three brain regions, including the cortex, hippocampus, and substantia nigra.

Figure 6C:
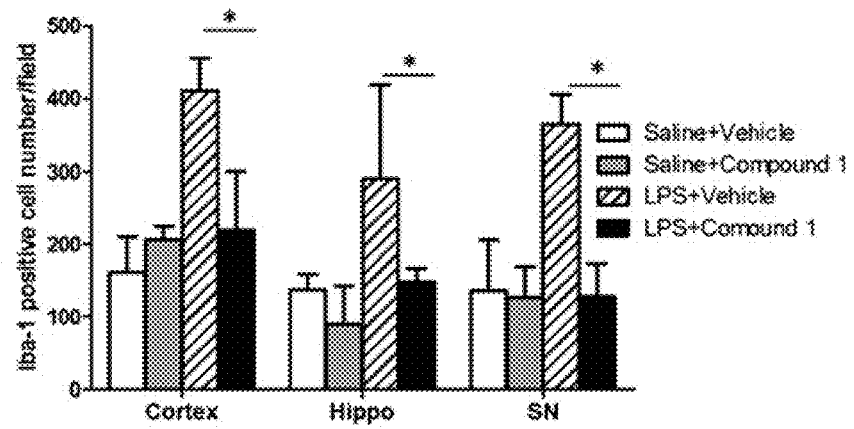
FIG. 6C shows the quantified results of FIG. 6B.

A quantitative analysis of Iba-1-stained cells in the different brain regions revealed that Compound 1 effectively blocked LPS-mediated hyper-activation of microglial cells (FIG. 6C).

Figure 6D:
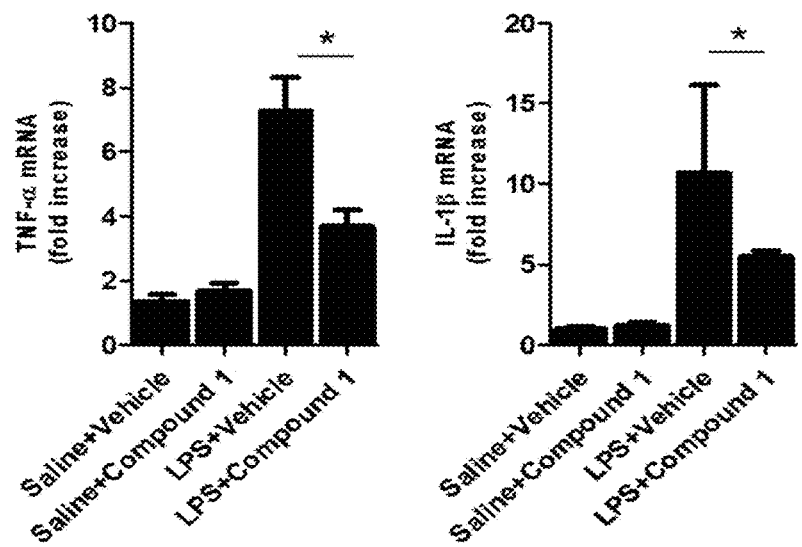
FIG. 6D shows the expression levels of proinflammatory genes (TNF-α, IL-1β) which were determined in the brain 72 h after the LPS injection by real-time RT-PCR. Levels of TNF-α and IL-1β mRNA were normalized to GAPDH levels and expressed as fold increase. *p<0.05 versus LPS+ vehicle-injected animals; analyzed by one-way ANOVA with Tukey's multiple comparison test. The data are expressed as mean±SD (n=3-4 per experimental group).

To confirm the anti-inflammatory effect of Compound 1 in vivo, proinflammatory cytokine expression levels were also measured in brain tissues after LPS and Compound 1 injection. The expression levels of TNF-α and IL-1β mRNA were significantly diminished by Compound 1 treatment in the inflammatory brain as measured by real-time RT-PCR (FIG. 6D).

What is claimed is:

1. A method for treating a neuroinflammatory disease, the method comprising the step of administering a compound represented by Chemical Formula 1 or a pharmaceutically acceptable salt thereof in an amount effective to treat a neuroinflammatory disease in a subject:

[Formula 1]

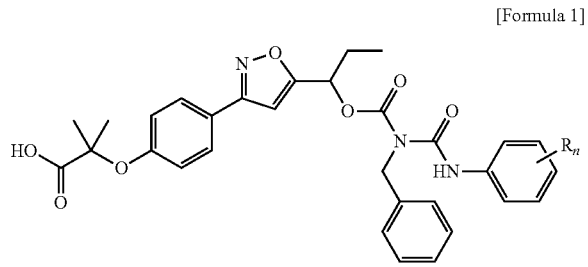

wherein
n is 1 or 2,
R is selected from the group consisting of C1-C4 alkoxy, C1-C4 alkyl unsubstituted or substituted by halogen, halogen, hydrogen, and 3,4-methylenedioxy, and
wherein the neuroinflammatory disease is selected from the group consisting of inflammatory brain disease, multiple sclerosis, Alzheimer's disease, Parkinson's disease, Huntington's disease, and amyotrophic lateral sclerosis.

2. The method of claim 1, wherein the compound of Chemical Formula 1 is selected from the group consisting of:
2-(4-(5-(1-((benzyl(phenylcarbamoyl)carbamoyl)oxy) propyl) isoxazol-3-yl)phenoxy)-2-methylpropanoic acid,
2-(4-(5-(1-((benzyl((2-methoxyphenyl)carbamoyl)carbamoyl) oxy)propyl)isoxazol-3-yl)phenoxy)-2-methylpropanoic acid,
2-(4-(5-(1-((benzyl((3-methoxyphenyl)carbamoyl)carbamoyl) oxy)propyl)isoxazol-3-yl)phenoxy)-2-methylpropanoic acid,
2-(4-(5-(1-((benzyl((4-methoxyphenyl)carbamoyl)carbamoyl) oxy)propyl)isoxazol-3-yl)phenoxy)-2-methylpropanoic acid,
2-(4-(5-(1-((benzyl((4-methylphenyl)carbamoyl)carbamoyl) oxy)propyl)isoxazol-3-yl)phenoxy)-2-methylpropanoic acid,
2-(4-(5-(1-((benzyl((4-trifluoromethylphenyl)carbamoyl) carbamoyl)oxy)propyl)isoxazol-3-yl)phenoxy)-2-methylpropanoic acid,
2-(4-(5-(1-((benzyl((4-chloromethylphenyl)carbamoyl) carbamoyl)oxy)propyl)isoxazol-3-yl)phenoxy)-2-methylpropanoic acid,
2-(4-(5-(1-((benzyl((4-n-butylmethylphenyl)carbamoyl) carbamoyl)oxy)propyl)isoxazol-3-yl)phenoxy)-2-methylpropanoic acid,
2-(4-(5-(1-((benzyl((3,4-dimethoxymethylphenyl)carbamoyl) carbamoyl)oxy)propyl)isoxazol-3-yl)phenoxy)-2-methylpropanoic acid, 2-(4-(5-(1-((benzyl((3,5-dimethoxymethylphenyl)carbamoyl) carbamoyl)oxy)propyl)isoxazol-3-yl)phenoxy)-2-methylpropanoic acid and 2-(4-(5-(1-((benzyl((3,5-methylenedioxymethylphenyl) carbamoyl)carbamoyl)oxy)propyl)isoxazol-3-yl)phenoxy)-2-methylpropanoic acid.

3. The method of claim 1, wherein the neuroinflammatory disease is inflammatory brain disease.

* * * * *

SEQUENCE LISTING

<160> NUMBER OF SEQ ID NOS: 10

<210> SEQ ID NO 1
<211> LENGTH: 25
<212> TYPE: DNA
<213> ORGANISM: Artificial Sequence
<220> FEATURE:
<223> OTHER INFORMATION: TNF-alpha forward

<400> SEQUENCE: 1
catcttctca aaattcgagt gacaa                                    25

<210> SEQ ID NO 2
<211> LENGTH: 21
<212> TYPE: DNA
<213> ORGANISM: Artificial Sequence
<220> FEATURE:
<223> OTHER INFORMATION: TNF-alpha reverse

<400> SEQUENCE: 2
acttgggcag attgacctca g                                        21

<210> SEQ ID NO 3
<211> LENGTH: 18
<212> TYPE: DNA
<213> ORGANISM: Artificial Sequence
<220> FEATURE:
<223> OTHER INFORMATION: IL-1 beta forward

<400> SEQUENCE: 3
gcaactgttc ctgaactc                                            18

<210> SEQ ID NO 4
<211> LENGTH: 18
<212> TYPE: DNA
<213> ORGANISM: Artificial Sequence
<220> FEATURE:
<223> OTHER INFORMATION: IL-1 beta reverse

<400> SEQUENCE: 4
ctcggagcct gtagtgca                                            18

<210> SEQ ID NO 5
<211> LENGTH: 25
<212> TYPE: DNA
<213> ORGANISM: Artificial Sequence
<220> FEATURE:
<223> OTHER INFORMATION: iNOS forward

<400> SEQUENCE: 5
cccttccgaa gtttctggca gcagc                                    25

<210> SEQ ID NO 6
<211> LENGTH: 25
<212> TYPE: DNA
<213> ORGANISM: Artificial Sequence
<220> FEATURE:
<223> OTHER INFORMATION: iNOS reverse

<400> SEQUENCE: 6
ggctgtcaga gcctcgtggc tttgg                                    25

<210> SEQ ID NO 7
<211> LENGTH: 20
<212> TYPE: DNA
<213> ORGANISM: Artificial Sequence

```
<220> FEATURE:
<223> OTHER INFORMATION: Ym-1 forward

<400> SEQUENCE: 7 gggcataacct ttatcctgag                                              20

<210> SEQ ID NO 8
<211> LENGTH: 20
<212> TYPE: DNA
<213> ORGANISM: Artificial Sequence
<220> FEATURE:
<223> OTHER INFORMATION: Ym-1 reverse

<400> SEQUENCE: 8
ccactgaagt catccatgtc                                               20

<210> SEQ ID NO 9
<211> LENGTH: 20
<212> TYPE: DNA
<213> ORGANISM: Artificial Sequence
<220> FEATURE:
<223> OTHER INFORMATION: GAPDH forward

<400> SEQUENCE: 9
accacagtcc atgccatcac                                               20

<210> SEQ ID NO 10
<211> LENGTH: 20
<212> TYPE: DNA
<213> ORGANISM: Artificial Sequence
<220> FEATURE:
<223> OTHER INFORMATION: GAPDH reverse

<400> SEQUENCE: 10
tccaccaccc tgttgctgta                                               20
```